Figure 1:
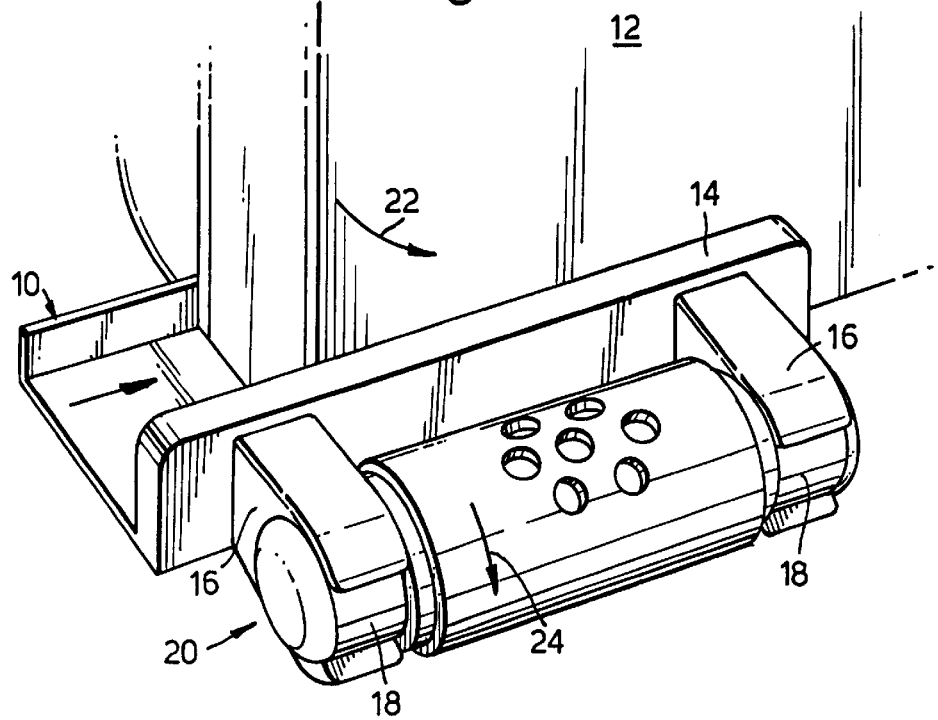

United States Patent
Johnson

[19]

[11] Patent Number: 5,873,529
[45] Date of Patent: Feb. 23, 1999

[54] DISPENSER FOR DEODORANTS OR THE LIKE

[75] Inventor: William Nevil Heaton Johnson, St. Peter Port, Channel Islands

[73] Assignee: Durand Limited, St. Peter Port, England

[21] Appl. No.: 624,456

[22] PCT Filed: Jul. 18, 1995

[86] PCT No.: PCT/GB95/01694

§ 371 Date: May 10, 1996

§ 102(e) Date: May 10, 1996

[87] PCT Pub. No.: WO96/04941

PCT Pub. Date: Feb. 22, 1996

[30] Foreign Application Priority Data

Aug. 9, 1994 [GB] United Kingdom ................... 9416030

[51] Int. Cl.$^6$ ............................ A62C 31/28; A24F 25/00
[52] U.S. Cl. ............................ 239/274; 239/34; 239/57; 239/60; 222/613
[58] Field of Search ................... 239/34, 57, 60, 239/274; 222/613, 614

[56] References Cited

U.S. PATENT DOCUMENTS

| 1,552,082 | 9/1925 | Riley ..................................... 239/60 X |
|---|---|---|
| 2,534,465 | 12/1950 | Marini ..................................... 239/274 |
| 2,746,798 | 5/1956 | Wardell, Jr. ............................ 239/274 |
| 3,043,523 | 7/1962 | Hogstrom ................................ 239/274 |
| 4,925,102 | 5/1990 | Jones et al. .......................... 239/57 X |
| 5,016,781 | 5/1991 | Wolde ................................. 239/274 X |
| 5,598,954 | 2/1997 | Salzano .................................. 239/274 |

FOREIGN PATENT DOCUMENTS

| A64768/90 | 4/1992 | Australia . |
|---|---|---|
| 2292528 | 6/1976 | France . |
| 2640163 | 6/1990 | France . |
| 7708737 | 2/1979 | Netherlands . |
| 2170541 | 8/1986 | United Kingdom . |

*Primary Examiner*—Andres Kashnikow
*Assistant Examiner*—Robin O. Evans
*Attorney, Agent, or Firm*—Arnold B. Silverman; Eckert Seamans Cherin & Mellott, LLC

[57] ABSTRACT

A device for distributing a deodorising, fragrancing insecticidal or the like product is arranged to be activated by opening and closing a room door. In one embodiment, the device comprises a spring plastics bracket 10 clipped to the bottom of a door and carrying spring clips 16 supporting for rotation a hollow plastics roller 20 containing a solid deodorant, fragrancing compound or insecticide, and having apertures in its wall to allow vaporised deodorant or the like to escape. The dispersal of the deodorant, fragrance or the like is promoted every time the door is opened and closed and so the rate of use of the deodorant, fragrancer or insecticide is appropriately related to room use.

11 Claims, 1 Drawing Sheet

DISPENSER FOR DEODORANTS OR THE LIKE

THIS INVENTION relates to a device adapted to expel into a room or to supply to a surface exposed within a room, a product, such as an air freshener or deodorant, insecticide or the like, in the form of a gas, vapour, vaporisable liquid or a spray.

Devices of this character are already known, but suffer from the disadvantage that they operate continuously or at intervals independent of the extent to which the room is used so that if a room is little used the amount of product supplied to the room is greatly in excess of what is required, whilst if the device is adapted to dispense the product at a rate appropriate to a room in average use, the amount of product dispensed in a given time may be inadequate for a room which is much used and into and from which people are continually passing. It is an object of the invention to provide a device of the kind specified which overcomes this disadvantage.

According to the invention there is provided a device adapted to be secured to a door to a room, or to a wall, floor or ceiling of a room adjacent a door, and arranged to expel into the room or to apply to a surface exposed within said room, a product in the form of a gas, vapour, vaporisable liquid or a spray, such as an air freshener or deodorant, insecticide, or the like, when the door is opened or closed.

Where the device is adapted to be secured to a door, the device preferably incorporates a roller arranged, when the device is appropriately secured to such door and the door is opened or closed, to run along a floor, ceiling, door frame or wall surface, the expulsion of said product being caused or permitted by such rotation.

In one embodiment, the device includes a bracket adapted to be clipped to a door edge, or otherwise to be secured to a door, adjacent the floor, an arm pivotally connected with the bracket carrying said roller at a free end thereof, with the arm being spring biassed relative to the bracket so that when the bracket is appropriately secured to a door, the arm is pulled into a position in which the roller bears upon the floor surface whereby when the door is open and closed, the roller is caused to run over the floor surface and is thereby caused to rotate.

In one embodiment, the roller may be of sponge rubber or plastics or other absorbent medium, and the product to be dispensed may be in the form of a gel or a wax-like medium impregnating the roller so that when the roller is rolled over the adjacent (e.g. floor) surface a controlled amount of the product will be delivered by the roller onto said surface.

In another arrangement, the arm may, for example, carry a reservoir of liquid to be dispensed, closed at its lower end by a permeable pad bearing upon the roller surface on the upper side of the roller, so that when the roller rolls over the floor, the roller is coated with the liquid and in turn applies such liquid to the floor surface to evaporate from the latter.

Alternatively, the product may comprise a block or stick of a wax or soap-like material incorporating the material to be dispensed in a similar manner. In this case, the roller may have a rough or absorbent surface, for example provided by foam plastics or the like whereby the roller, in the region of its surface, will be impregnated with the product to be dispensed when the roller is rolled over the floor surface and the product or the active ingredient of the product can subsequently, over a brief period following the opening and closing of the door, allow the product to evaporate therefrom over a short period of time.

It will be appreciated that other arrangements are possible. For example, rotation of the roller along the floor surface may serve to cock a spring mechanism operating a pump to dispense the product into the atmosphere or to actuate briefly an aerosol mounted on the device.

If desired, the device may incorporate a catch which can be operated manually or by foot, to inhibit rotation of the roller and to cause the device to act as a door stop.

In further variants, the device may be adapted to be secured to a wall surface adjacent a door, so that a mechanical product-dispensing action is produced when the door is opened by engagement of the door with a movable part of the device. Indeed, in further variants, the device may simply comprise means for detecting when a door is opened or closed, for example electronic sensing means and for causing an electrically or otherwise operated device in the room to dispense the desired product in response to the opening and closing of the door. Advantageously, in any event, the product is arranged to be dispensed in the vicinity of the free edge of the door so that the draught produced during opening and closing of the latter assists in dispersing the product throughout the room.

Figure 2:
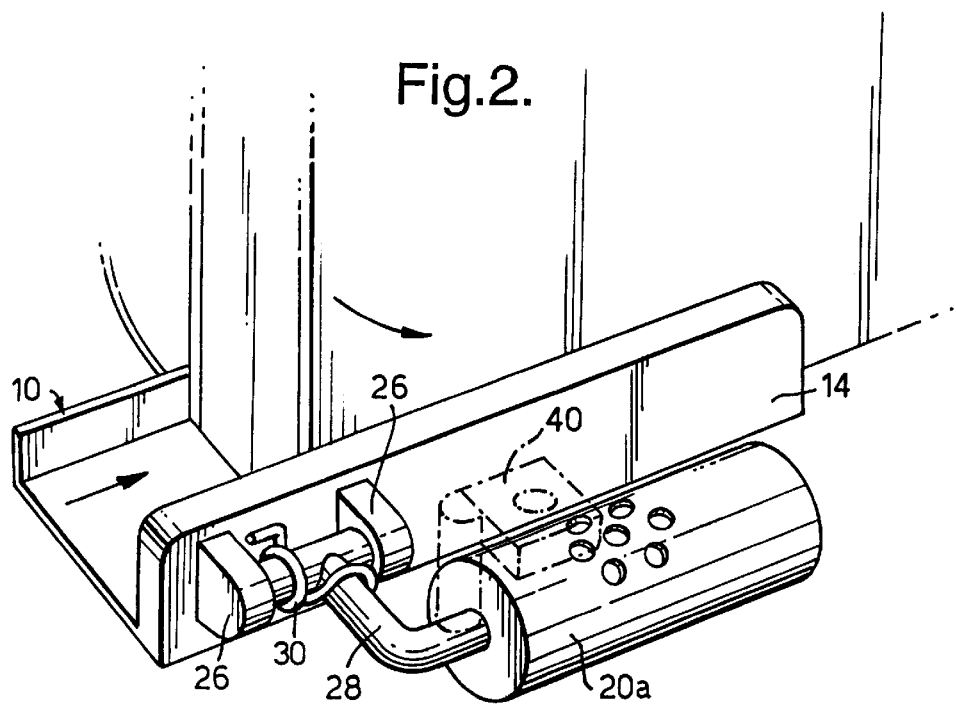

Embodiments of the invention are described below by way of example with reference to the accompanying drawings, in which:

FIG. 1 is a perspective view illustrating one embodiment being fitted to a door, and FIG. 2 is a similar perspective view of a variant.

Referring to FIG. 1, the device shown comprises a bracket 10 in the form of a resilient plastics channel of a width corresponding to the thickness of a standard door 12 and adapted to be sprung around the lower edge of the door and slid along the door until its end lies flush with the free vertical edge of the door or lies inwardly from said free edge towards the hinges. One vertical wall 14 of the channel 10 carries plastics spring clips 16 having generally C-shaped spring formations affording respective concave journal surfaces each extending over rather more than 180°. These clips 16 receive respective cylindrical bearing surfaces 18 at respective ends of a replaceable plastics roller 20, so that when the roller 20 is fully inserted into the clips 16 it is free to rotate therein, with its lower surface resting on the floor surface adjacent the door, so that when the door is swung in the direction indicated by arrow 22, the roller 24 will roll over the floor in the sense indicated by arrow 24 and vice versa. The roller 20 may comprise, as illustrated, a hollow central portion containing a solid vaporisable air freshener or fragrancing medium, insecticide or the like, the cylindrical wall of said hollow portion being perforated by apertures, as illustrated, to allow vaporised air-freshener, fragrance, insecticide or the like to escape. When the air freshener, fragrancing medium, insecticide or the like is exhausted, the roller 20 is simply pulled out of the spring clips 16 and a fresh roller 20 installed in its place.

In the arrangement shown, the central region of the roller 20 is of greater diameter than the cylindrical bearing surfaces at the ends of the roller, so that the central portion of the roller also serves to locate the roller axially with respect to the clips 16.

Referring to FIG. 2, in which parts corresponding to parts in FIG. 1 have like references, the wall 14 of bracket 10 carries, instead of clips 16, bearing blocks 26 pivotally supporting an arm 28 carrying rotatably a roller 20a at a free end thereof, with the arm 28 being spring biassed by a spring 30 relative to the bracket 10 so that when the bracket is secured to a door, the arm 28 is pulled into a position in which the roller 20a bears upon the floor surface whereby when the door is open and closed, the roller is caused to run over the floor surface and is thereby caused to rotate.

The roller 20a may, like the roller 20, be in the form of a hollow plastics cylinder containing a solid deodorant, fragrancing medium, insecticide or the like.

In another arrangement, the arm 28 may, for example, carry a reservoir of liquid to be dispensed, closed at its lower end by a permeable pad bearing upon the roller surface on the upper side of the roller, so that when the roller rolls over the floor, the roller is coated with the liquid and in turn applies such liquid to the floor surface to evaporate from the latter. Such a reservoir is indicated in dotted lines at 40 in FIG. 1.

I claim:

1. A device adapted to be secured to a door to a room, and to expel a product when said door is opened or closed, said device comprising a roller being structured to engage and rotate along a floor surface when said door is opened or closed and means to effect expulsion of said product responsive to said rotation of said roller along the floor surface, wherein said roller is hollow, having an outer wall, and said product is initially stored within said hollow roller, said means to effect expulsion expelling said product as a vapor or spray upon said rotation of said roller.

2. A device according to claim 1, wherein said outer wall is provided with a plurality of apertures therethrough to allow said vapor or spray to be expelled therethrough.

3. A device adapted to be secured to a door to a room, and to expel a product when said door is opened or closed, said device comprising a roller being structured to engage and rotate along a floor surface when said door is opened or closed and means to effect expulsion of said product responsive to said rotation of said roller along the floor surface, including said means to effect expulsion having means to apply said product to a surface of said roller during said rotation to thereby effect subsequent application of said product to the floor surface by said roller.

4. A device according to claim 3, wherein said product is in the form of a substantially solid block in engagement with the roller surface and said roller surface is roughened such that upon rotation, the roller surface becomes impregnated with said product which is subsequently applied to the floor surface.

5. A device according to claim 3, wherein said product is in substantially liquid form, and a reservoir initially containing said liquid being in communication with said roller surface, whereby upon rotation of said roller said liquid product is applied to said roller surface and subsequently applied to the floor surface.

6. A device according to claim 5, wherein said roller surface comprises an absorbent material.

7. A device adapted to be secured to a door to a room, and to expel a product when said door is opened or closed, said device comprising a roller being structured to engage and rotate along a floor surface when said door is opened or closed and means to effect expulsion of said product responsive to said rotation of said roller along the floor surface, further comprising a bracket in the form of a channel adapted to fit around a lower edge of said door, further provided with an arm pivotally connected with said bracket, carrying said roller at the free end thereof.

8. A device according to claim 7, wherein said arm is spring biased relative to the bracket, such that the arm is pulled into a position in which the roller bears upon the floor surface.

9. A device adapted to be secured to a door to a room, and to expel a product when said door is opened or closed, said device comprising a roller being structured to engage and rotate along a floor surface when said door is opened or closed and means to effect expulsion of said product responsive to said rotation of said roller along the floor surface, and a bracket in the form of a channel adapted to fit around a lower edge of said door.

10. A device according to claim 9, wherein said product is an air freshener.

11. A device according to claim 9, wherein said product is an insecticide.

* * * * *